United States Patent
Garrett

(10) Patent No.: US 10,183,073 B1
(45) Date of Patent: Jan. 22, 2019

(54) METHOD OF MAKING A VACCINE

(71) Applicant: Hyper Light Technologies, LLC, Nashville, NC (US)

(72) Inventor: Kurt A. Garrett, Raleigh, NC (US)

(73) Assignee: Hyper Light Technologies, LLC, Nashville, NC (US)

( * ) Notice: Subject to any disclaimer, the term of this patent is extended or adjusted under 35 U.S.C. 154(b) by 0 days.

(21) Appl. No.: 16/145,962

(22) Filed: Sep. 28, 2018

Related U.S. Application Data

(63) Continuation-in-part of application No. 15/720,336, filed on Sep. 29, 2017.

(51) Int. Cl.
| | |
|---|---|
| *C12N 15/01* | (2006.01) |
| *A61K 39/245* | (2006.01) |
| *C12N 7/00* | (2006.01) |
| *A61P 31/22* | (2006.01) |

(52) U.S. Cl.
CPC ........... *A61K 39/245* (2013.01); *A61P 31/22* (2018.01); *C12N 7/00* (2013.01); *C12N 2700/00* (2013.01); *C12N 2710/16631* (2013.01); *C12N 2710/16661* (2013.01)

(58) Field of Classification Search
CPC .................................................. A61K 39/245
See application file for complete search history.

(56) References Cited

U.S. PATENT DOCUMENTS

| | | |
|---|---|---|
| 6,303,130 B1 | 10/2001 | Purdy et al. |
| 9,801,966 B2 | 10/2017 | Garrett |
| 9,961,927 B2 | 5/2018 | Garrett |

OTHER PUBLICATIONS

"New chlamydia vaccine shows promise after being tested on mice." NHS Choices, Jun. 19, 2015, https://www.nhs.uk/news/medication/new-chlamydia-vaccine-shows-promise-after-being-tested-on-mice/.

*Primary Examiner* — Albert M Navarro
(74) *Attorney, Agent, or Firm* — James G. Passé; Passé Intellectual Property, LLC

(57) ABSTRACT

A method of producing attenuated cells for a mammalian vaccine comprising killing or attenuating the cells with a high energy, low heat UV light.

5 Claims, No Drawings

METHOD OF MAKING A VACCINE

This application is a continuation-in-part of U.S. non-provisional patent application Ser. No. 15/720,336 filed on Sep. 29, 2017, which is incorporated herein in its entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to a method and system for making vaccines. In particular, it relates to creating attenuated cells for creating a vaccine in large quantities, especially useful for use in individually produced vaccines. It also is a method for creating antibodies.

Description of Related Art

The production of a vaccine and its usefulness are well-known. An infectious cell is attenuated but not so destroyed that it does not still create an immune response, producing antibodies without causing the user to contract the disease. While such an approach does not work with all infectious cells, its usefulness is unquestionable.

One of the biggest problems is the process of killing the cells without damage. Even more problematic is the time it takes to kill the cells can be drawn out leading to long lead times for producing large quantities of vaccine, especially during outbreaks such as the flu or the like. One version of the attenuation process is the exposure of *P haemolytica* to UV irradiation for 60 minutes using low level UV irradiation. Since temperatures, as taught in the art, need to be around 58 degrees F. or less, exposure to high energy UV irradiation is out of the question because of the high heat generated. Further, it is not known if such high energy UV will damage cellular proteins and carbohydrates necessary to create an immune response. Accordingly, the current UV low energy practice is not widely utilized, if at all.

BRIEF SUMMARY OF THE INVENTION

The present invention relates to the use of high energy, low heat UV source for the production of an antibody response, i.e. vaccine production or portions thereof (e.g. isolated antibodies). It is discovered that such process takes mere seconds rather than an hour or more leading to rapid production of vaccines from live cell cultures. Such cells can then be introduced into patients as vaccines or to stimulate additional antibody production in an already infected individual.

Accordingly, in one embodiment, there is a method of producing attenuated infectious cells comprising:
a) isolating a plurality of infectious cells;
b) selecting a high energy UV light source that delivers a low heat UV containing light to the end of a light guide; and
c) exposing the infectious cells to the light from the end of the light guide at sufficient distance and time to kill the cells without damaging cellular proteins and carbohydrates to produce attenuated cells.

In another embodiment, there is a composition comprising a vaccine with attenuated infectious cells made from exposure to a high energy UV light source that delivers a low heat UV containing light to the end of a light guide.

In another embodiment, there is a method of producing a vaccine to a select virus comprising:
a) select viable virus cells containing one or more different viruses and separate them into a plurality of separate samples;
b) select a high energy, low heat UV source and position it from about 0.0 to about 1 inch from the cells in each sample;
c) position an IR filter such that it removes infrared energy from the UV source;
d) treat the cells in each sample to UV light from the UV light source for a period of between about 0.1 second to about 2 minutes; and
e) test each of the samples in an animal model to determine the most effective sample result and selecting the samples that provide full protection when challenged with the virus of the cells.

DETAILED DESCRIPTION OF THE INVENTION

While this invention is susceptible to embodiment in many different forms, there is shown in the drawings, if any, and will herein be described in detail, specific embodiments with the understanding that the present disclosure of such embodiments is to be considered as an example of the principles and not intended to limit the invention to the specific embodiments shown and described. In the description below, like reference numerals are used to describe the same, similar, or corresponding parts in the several views of the drawings, if any. This detailed description defines the meaning of the terms used herein and specifically describes embodiments in order for those skilled in the art to practice the invention.

DEFINITIONS

The terms "about" and "essentially" mean±10 percent.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language and is so intended.

Reference throughout this document to "one embodiment", "certain embodiments", "an embodiment", or similar terms means that a particular feature, structure, or characteristic described in connection with the embodiment is included in at least one embodiment of the present invention. Thus, the appearances of such phrases in various places throughout this specification are not necessarily all referring to the same embodiment. Furthermore, the particular features, structures, or characteristics may be combined in any suitable manner in one or more embodiments without limitation.

The term "or", as used herein, is to be interpreted as an inclusive or meaning any one or any combination. Therefore, "A, B, or C" means any of the following: "A; B; C; A and B; A and C; B and C; A, B, and C". An exception to this definition will occur only when a combination of elements, functions, steps, or acts are in some way inherently mutually exclusive.

The drawings featured in the figures, if any, are for the purpose of illustrating certain convenient embodiments of the present invention and are not to be considered as limitation thereto. The term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein, and use of the term "means" is not intended to be limiting.

As used herein, the term "attenuated" refers to a virus or bacterium or other pathogen that has been modified to reduce its virulence to the infection the cell would cause while maintaining the virus or bacteria's ability to cause an immune response. The cell can either be alive or dead. The term "live attenuated vaccine" is one which the cells remain viable for infecting and replicating within a target host. The present invention can be used to modify a wide variety or viruses, e.g. adenovirus, measles, mumps, rubella, influenza, chicken pox, smallpox, polio, rotavirus, yellow fever, chikungunya, hantavirus, cytomegalovirus, dengue, Epstein-Barr virus, hepatitis A, B, C, or E, human papilloma virus, encephalitis, HIV, and rabies, to name a few. Attenuated vaccines can be formulated for use in mammals, e.g. humans. Furthermore, the present invention can be designed, following the teachings herein, to be grown in an avian system for use as a vaccine in a mammalian, vice versa, or using other viral expression system (e.g. insect cells) for use in non-insects. Bacteria for use could include, but is not limited to, *staphylococcus aureus, bacillus athracis, treponema pallidum, strepococcus, nesseria meningitis, escherichia coli, pseudomonas aeruginosa, tuberculosis, haemophila influenzae, enterococci faecalis, clostridium difficile, legionella, listeria, salmonella, clostridia, leptospira, borellia, helicobacter pylori*, and the like.

As used herein, the term "vaccine", "vaccination", and "vaccinating" refer to compositions and methods for modulating an immune response to a selected antigen such that the response is more efficient, more rapid, greater in magnitude, and/or more easily induced.

As used herein, the term "modulating an immune response" refers to the stimulation and/or activation of an immune response to a selected antigen, but it also refers to the suppression, elimination, or attenuation of an immune response to a selected antigen.

As used herein, the "antigen" refers to a molecule that can initiate a humoral and/or a cellular immune response in a recipient to the antigen. Antigens can be any type of biologic molecule including, for example, simple intermediary metabolites, sugars, lipids, and hormones as well as macromolecules such as complex carbohydrates, phospholipids, nucleic acids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, and other miscellaneous antigens.

The compositions, vaccines, or formulations of the invention can be used, for example, to modulate an immune response in a mammal such as a human. Vaccination with infectious cell attenuated vaccines (LAVs) is an effective way for prevention of infectious disease.

As used herein, the term "infectious cells" refers to a whole-cell pathogen with intact DNA.

As used herein, the term "isolating a plurality of infectious cells" refers to whole-cell pathogens either homogenous or heterogenous.

As used herein, the term "high intensity UV light source that delivers a low heat UV light" refers to a device that has a light source producing a spectrum of UV light capable of killing a microorganism, such as taught in U.S. Pat. No. 9,801,966 issued on Oct. 31, 2017 in the name of Kurt A. Garrett and U.S. Pat. No. 9,961,927 issued on May 8, 2018 in the name of Kurt A. Garrett. In particular, it produces a wide UV spectrum (i.e. more than just an isolated wavelength) even though it can produce other spectrums of light and, in one embodiment, the light produces a high UV output. It consists of a high intensity light and a dichroic reflector which focuses the light and removes heat and then delivers the UV light to a light tube where the light coming out of the far end of the light tube is used to kill cancer cells without damaging underlying physical structure thus minimizing or eliminated damage to healthy cells near the cancer cells.

As used herein, the "high intensity light" refers to a bulb of any kind which produces a sterilizing UV light. This can be UVA, UVB, UVC, or a combination. Regular bulbs, but also high intensity discharge (HID) bulbs, are also embodiments of the invention. So, for example, a high intensity mercury xenon (HgXe) bulb can be utilized. These types of bulbs are high UV output bulbs. In general, the light output of some bulbs of the invention is from about $0.1$ $J/cm^2$ to about $50.0$ $J/cm^2$. It also includes arc type lamps when they are focused properly to the light tube.

As used herein, the term "high intensity light" refers to light output of about at least 80 lumens per watt output. In order to achieve this high intensity light output, one cannot use low or medium pressure lamps that produce UV light, as they do not produce enough light output. In order to achieve the high intensity output needed, one can add to the arc discharge lamp's light output an elliptical reflector which collimates the polychromatic light into still greater intensity (intensity being understood as energy per area) of about 100 lumens per watt (i.e. producing the high intensity light output needed).

As used herein, the term "dichroic reflector" refers to any of a dichroic focus, reflector, mirror, lens, or the like that takes light from the light source and allows some or all of the thermal energy to pass through the reflector while taking the light, especially the UV light, to be reflected for focusing. In one embodiment, there may be more than one dichroic reflector but at least one must focus the light to the light pipe. The dichroic reflector can be any shape that works to either remove heat or focus the light, but, in one embodiment, it is an elliptical shape for focusing. In one embodiment, an elliptical dichroic reflector is used with an arc lamp. This is different from a dichroic filter which only filters or reflects light but does not pass heat wavelengths through it. The dichroic filter can be a powered or unpowered device.

As used herein, the term "polychromatic" refers to light comprising multiple wavelengths of light.

As used herein, the term "sufficient distance and time" refers to the time period and distance from the cells that light produced by the device is exposed (light shining on it) to a cell in order to kill it. In one embodiment, it is from about 0.01 second to about 5 seconds. In one embodiment, a shutter is utilized to open, close, and modulate the passage of light from the light source to the cell. The exposure can be directly from the end of the light tube or extended via a light fiber at the end of the light tube, especially for insertion of the fiber into a cell tumor either directly or through the skin of the animal or human.

Following irradiation, cells are prepared for administration as a vaccine by formulation in an effective immunization dosage with a pharmaceutically acceptable carrier. An effective immunization dosage is defined herein as being that amount which will induce complete or partial immunity (elicit a protective immune response) in a treated animal against subsequent challenge with virulent cells. Immunity is considered as having been induced in a population of treated mammals when the level of protection for the population is significantly higher than that of an unvaccinated control group. The appropriate effective dosage can be readily determined by the practitioner skilled in the art.

The cells are prepared for administration by formulation in a pharmaceutically acceptable carrier such as physiological saline, mineral oil, vegetable oils, aqueous sodium carboxymethyl cellulose, or aqueous polyvinylpyrrolidone. The vaccine formulations may also contain optional adjuvants, antibacterial agents, or other pharmaceutically active agents as are conventional in the art. Without being limited thereto, suitable adjuvants include, but are not limited to, mineral oil, vegetable oils, alum, Freund's incomplete adjuvant, and Freund's incomplete adjuvant with oils being embodiments. Still other preferred adjuvants include microparticles or beads of biocompatible matrix materials. The microparticles may be composed of any biocompatible matrix materials as are conventional in the art including, but not limited to, agar and polyarylate. The practitioner skilled in the art will recognize that other carriers or adjuvants may be used as well.

In accordance with a preferred embodiment, the cells may be incorporated into microparticles or microcapsules to prolong the exposure of the antigenic material to the subject animal and hence protect the animal against infection for long periods of time. The microparticles and capsules may be formed from a variety of well-known inert, biocompatible matrix materials using techniques conventional in the art. Without being limited thereto, suitable matrix materials include natural or synthetic polymers such as alginates, poly(lactic acid), poly(lactic/glycolic acid), poly(caprolactone), polycarbonates, polyamides, oxide, and particularly agar and polyacrylates.

The vaccines of the invention may be administered to the subject mammal intramuscular or transthoracic injection, or by aerosol. However, subcutaneous injection is preferred for practical considerations. The vaccine may be administered in a single dose or in a plurality of doses. In accordance with a preferred embodiment, the vaccine may be administered in two doses about 2 to 6 weeks apart, most preferably about 2-3 weeks apart. The subject animals may be vaccinated at any time, although it is preferred to administer the vaccine shortly (optimally about 10 days to two weeks) before periods of anticipated stress, such as during shipping or other handling. It is also envisioned that the vaccine may be administered to pregnant animals prior to birth to increase production of hyper-immune colostrum.

Accordingly, in the practice of the invention, selected infectious cells which have an antigen or other chemical which elicits an immune response in a mammal is isolated using methods known in the art. The high energy UV light source that delivers a low heat UV containing light to the end of the light guide is selected, for example, such as shown in U.S. Pat. No. 9,801,966 issued on Oct. 31, 2017 in the name of Kurt A. Garrett and U.S. Pat. No. 9,961,927 issued on May 8, 2018 in the name of Kurt A. Garrett. The light is used to kill or at least render the cell non-deleterious. Since exposure times are a matter of seconds rather than minutes, large quantities of cells can be treated in a short period of time. For example, a conveyor belt type system could be utilized or the light on a robotic arm could cover large areas of surface in a meticulous manner.

As used herein, the term "virus" refers to an infective agent that typically consists of a nucleic acid molecule in a protein coat and is too small to be seen by light microscopy and is able to multiply within living cells of a host. Typically, it refers to viruses that have a detrimental effect on animals or humans.

As used herein, the term "HSV 2" refers to the herpes simplex virus.

EXAMPLES

Example 1

First, obtain viable HSV 2 cells, the target. Position the UV device light guide 0.5-1 inch from the target. Dial in exposure times of 12 duplicate labeled samples 1-A and 1-B, 2-A and 2-B, etc. of predetermined HSV 2 PFU from 0.1 sec incrementally to 2 min. Rinse the samples. Take an aliquot of each sample B and inject into a suitable animal model. Over the next week to three weeks, take sample of the animal blood. Test the blood for antibodies. It is expected that antibodies will increase in some samples more than others. Record other relevant observations especially changes that would indicate adverse reactions. After antibodies levels plateau, select candidates from the animal cohort for control and full test. Prior to full test, attempt to grow A samples 1-12 in-vitro over 72 hours. Record the results. Continue with the full test. Make observations. It is expected that most cohorts will have some immunity while others will present full protections when challenged with the virus of the HSV 2 cells.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings, if any. Consequently, while the present invention has been described with reference to particular embodiments, modifications of structure, sequence, materials, and the like apparent to those skilled in the art still fall within the scope of the invention as claimed by the applicant.

What is claimed is:

1. A method of producing a vaccine to a select virus comprising:
   a) select viable virus cells containing one or more different viruses and separate them into a plurality of separate samples;
   b) select a high energy, low heat UV source and position it from about 0.0 to about 1 inch from the cells in each sample;
   c) position an IR filter such that it removes infrared energy from the UV source;

d) treat the cells in each sample to UV light from the UV light source for a period of between about 0.1 second to about 2 minutes; and e) test each of the samples in an animal model to determine the most effective sample result and selecting the samples that provide full protection when challenged with the virus of the cells.

2. The method according to claim 1 wherein the treated cells are formulated into a vaccine.

3. The method according to claim 2 wherein the vaccine is administered to a mammal in a sufficient amount to elicit an immune response that creates antibodies to the infectious cells.

4. The method according to claim 1 wherein the cells are exposed to the light from about 0.1 second to about 5 seconds.

5. The method according to claim 1 wherein the virus is HSV 2.

* * * * *